US00PP28408P3

(12) United States Plant Patent
Brand et al.

(10) Patent No.: US PP28,408 P3
(45) Date of Patent: Sep. 19, 2017

(54) ***BUDDLEIA* PLANT NAMED 'UCONNBD603'**

(50) Latin Name: *Buddleia davidii*
Varietal Denomination: UCONNBD603

(71) Applicant: UNIVERSITY OF CONNECTICUT, Farmington, CT (US)

(72) Inventors: Mark Henry Brand, Willington, CT (US); William Addison Smith, Bristol, CT (US)

(73) Assignee: University of Connecticut, Farmington, CT (US)

( * ) Notice: Subject to any disclaimer, the term of this patent is extended or adjusted under 35 U.S.C. 154(b) by 138 days.

(21) Appl. No.: 14/545,688

(22) Filed: Jun. 6, 2015

(65) Prior Publication Data

US 2016/0360666 P1 Dec. 8, 2016

(51) Int. Cl.
*A01H 5/00* (2006.01)

(52) U.S. Cl.
USPC ..... Plt./242

(58) Field of Classification Search
USPC ..... Plt./226, 242
See application file for complete search history.

(56) References Cited

PUBLICATIONS

PLUTO: Plant Variety Database, Dec. 8, 2016, citation for 'uconnbd603'.*

* cited by examiner

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Buddleia* plant named 'UCONNBD603', characterized by its relatively compact, upright and outwardly spreading plant habit; freely branching habit and thick stems with short internodes; dense and bushy appearance; leathery and durable leaves; freely flowering habit; broadly conical inflorescences with numerous white-colored flowers; and good garden performance.

1 Drawing Sheet

FEDERALLY SPONSORED RESEARCH OR DEVELOPMENT

This invention was made with government support under grant number 2015-31200-06009 awarded by the United States Department of Agriculture. The United States Government has certain rights in the invention.

Botanical designation: *Buddleia davidii.*

Cultivar denomination: 'UCONNBD603'.

BACKGROUND OF THE INVENTION

The present invention relates to a new and distinct *Buddleia* plant, botanically known as *Buddleia davidii* and hereinafter referred to by the name 'UCONNBD603'.

The new *Buddleia* plant is a product of a planned breeding program conducted by the Inventors in Storrs, Conn. The objective of the breeding program was to create new compact *Buddleia* plants with dense growth habit and attractive flower coloration.

The new *Buddleia* plant originated from a cross-pollination conducted by the Inventors in July, 2008 in Storrs, Conn. of a proprietary selection of *Buddleia davidii* identified as code designation Uconn dwf-01, not patented, as the female, or seed, parent with *Buddleia davidii* 'White Profusion', not patented, as the male, or pollen, parent. The new *Buddleia* plant was discovered and selected by the Inventors as a single flowering plant within the progeny of the stated cross-pollination in a controlled environment in Storrs, Conn. in July, 2010.

Asexual reproduction of the new *Buddleia* plant by softwood stem cuttings in a controlled environment in Storrs, Conn. since July, 2010 has shown that the unique features of this new *Buddleia* plant are stable and reproduced true to type in successive generations.

SUMMARY OF THE INVENTION

Plants of the new *Buddleia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'UCONNBD603 '. These characteristics in combination distinguish 'UCONNBD603' as a new and distinct *Buddleia* plant:

1. Relatively compact, upright and outwardly spreading plant habit.
2. Freely branching habit, thick stems with short internodes; dense and bushy appearance.
3. Leathery and durable leaves.
4. Freely flowering habit.
5. Broadly conical inflorescences with numerous white-colored flowers.
6. Good garden performance.

Plants of the new *Buddleia* differ primarily from plants of the female parent selection in the following characteristics:

1. Plants of the new *Buddleia* have larger inflorescences than plants of the female parent selection.

2. Plants of the new *Buddleia* have white-colored flowers whereas plants of the female parent selection have dark lilac-colored flowers.

Plants of the new *Buddleia* differ primarily from plants of the male parent, 'White Profusion', in the following characteristics:

1. Plants of the new *Buddleia* are more compact than plants of 'White Profusion'.
2. Plants of the new *Buddleia* have thicker stems, shorter internodes and are denser and bushier than plants of 'White Profusion'.
3. Plants of the new *Buddleia* have broader and darker green-colored leaves than plants of 'White Profusion'.
4. Inflorescences of plants of the new *Buddleia* are broader, fuller and denser than inflorescences of plants of 'White Profusion'.

Plants of the new *Buddleia* can also be compared to plants of *Buddleia davidii* 'ILVOargus01', not patented. In side-by-side comparisons, plants of the new *Buddleia* differ primarily from plants of 'ILVOargus01' in the following characteristics:

1. Plants of the new *Buddleia* are more compact than plants of 'ILVOargus01'.
2. Inflorescences of plants of the new *Buddleia* face more outwardly than inflorescences of plants of 'ILVOargus01'.
3. Inflorescences of plants of the new *Buddleia* are fuller and denser than inflorescences of plants of 'ILVOargus01'.

BRIEF DESCRIPTION OF THE PHOTOGRAPH

The accompanying colored photograph illustrates the overall appearance of the new *Buddleia* plant showing the colors as true as it is reasonably possible to obtain in colored reproductions of this type. Colors in the photograph may differ slightly from the color values cited in the detailed botanical description which accurately describe the colors of the new *Buddleia* plant.

The photograph is a close-up view of a typical flowering plant of 'UCONNBD603' grown in an outdoor nursery.

DETAILED BOTANICAL DESCRIPTION

The aforementioned photograph and following observations, measurements and values describe plants grown during the summer in ground beds in an outdoor nursery in Grand Haven, Mich. and under cultural practices typical of commercial production. Plants were two years old when the photograph and description were taken. During the production of the plants, day temperatures ranged from 18° C. to 27° C. and night temperatures ranged from 5° C. to 10° C. In the following description, color references are made to The Royal Horticultural Society Colour Chart, 1995 Edition, except where general terms of ordinary dictionary significance are used.

Botanical classification: *Buddleia davidii* 'UCONNBD603'.

Parentage:

*Female, or seed, parent.*—Proprietary selection of *Buddleia davidii* identified as code designation Uconn dwf-01, not patented.

*Male, or pollen, parent.*—*Buddleia davidii* 'White Profusion', not patented.

Propagation:

*Type.*—By softwood stem cuttings.

*Time to initiate roots plant, summer.*—About one to two weeks at temperatures ranging from 21° C. to 29° C.

*Time to produce a rooted plant, summer.*—About 30 days at temperatures ranging from 21° C. to 29° C.

*Root description.*—Medium in thickness, fibrous; white in color.

*Rooting habit.*—Freely branching; dense.

Plant description:

*Plant and growth habit.*—Deciduous perennial shrub; relatively compact, upright and outwardly spreading plant habit; thick stems, short internodes and dense and bushy appearance; vigorous growth habit.

*Plant height.*—About 50 cm.

*Plant width (spread).*—About 64.5 cm.

*Lateral branches.*—Quantity: Freely branching habit with about six primary lateral branches developing per plant; pinching enhances lateral branch development. Length: About 49.5 cm. Diameter: About 8 mm. Internode length: About 3 cm. Strength: Strong. Aspect: Erect to about 45° from vertical. Texture: Pubescent, glaucous; with development, woody. Color, developing: Close to 145C. Color, developed: Close to 199B with striations, close to 199A.

Leaf description:

*Arrangement and appearance.*—Opposite, simple; leaves durable and leathery.

*Length.*—About 12 cm.

*Width.*—About 3.2 cm.

*Shape.*—Lanceolate.

*Apex.*—Acute to acuminate.

*Base.*—Cuneate.

*Margin.*—Serrulate; slightly undulate.

*Texture, upper and lower surfaces.*—Pubescent, coriaceous; venation prominent.

*Venation pattern.*—Pinnate.

*Color.*—Developing and fully expanded leaves, upper surface: Close to 139A; venation, close to 145A. Developing and fully expanded leaves, lower surface: Close to 194A; venation, close to 145B.

*Petioles.*—Length: About 3 mm. Diameter: About 2 mm. Texture, upper and lower surfaces: Pubescent. Color, upper surface: Close to 145A. Color, lower surface: Close to 146C.

Flower description:

*Flower type and flowering habit.*—Single salverform flowers arranged on terminal and axillary panicles; inflorescences face mostly outwardly; panicles broadly conical in shape; freely flowering habit with more than 1,250 flowers developing per inflorescence; flowers not persistent.

*Fragrance.*—Fragrant; sweet, honey-like, pleasant.

*Natural flowering season.*—Long flowering period, plants flower continuously from mid-summer into the autumn in Michigan.

*Flower buds.*—Height: About 7 mm. Diameter: About 1 mm. Shape: Lanceolate. Color: Close to 155B.

*Inflorescence length.*—About 13 cm to 17 cm.

*Inflorescence diameter.*—About 5 cm.

*Flower diameter.*—About 5 mm.

*Flower depth.*—About 8 mm.

*Petals.*—Quantity per flower: Typically four in a single whorl. Length: About 2 mm. Width: About 2 mm. Shape: Oblong to obovate. Apex: Obtuse. Base:

Slightly acute. Margin: Entire; slightly undulate giving a ruffled appearance. Texture, upper and lower surfaces: Smooth, glabrous; soft. Color: Developing and fully developed petals, upper surface: Close to 155B; color does not change with development. Developing and fully developed petals, lower surface: Close to 155B; color does not change with development. Throat: Close to 31A. Tube: Close to 155B.

*Sepals.*—Quantity per flower: Typically five in a single whorl. Length: About 2 mm. Width: About 0.5 mm. Shape: Lanceolate to ovate. Apex: Acute. Base: Cuneate. Margin: Entire. Texture, upper and lower surfaces: Slightly pubescent. Color, upper surface: Towards the base, close to 145C and towards the apex, close to 147C. Color, lower surface: Close to 148D.

*Pedicels.*—Length: About 1 mm to 5 mm. Diameter: About 0.5 mm. Strength: Strong. Angle: Upright to outwardly. Texture: Pubescent to smooth and glabrous. Color: Close to 145B tinged with close to 184A.

*Reproductive organs.*—Stamens: Quantity per flower: Typically four. Filament length: About 0.6 mm. Filament color: Close to 155B tinged with close to 145B. Anther length: About 1 mm. Anther shape: Oblong. Anther color: Close to 155B. Pollen amount: Scarce. Pollen color: Close to 11C. Pistils: Quantity per flower: One. Pistil length: About 1 mm. Stigma shape: Oblong. Stigma color: Close to 145A.

*Seeds and fruits.*—Quantity of fruit per lateral branch: More than 100. Fruit length: About 7 mm to 9 mm. Fruit diameter: About 2 mm. Fruit texture: Smooth. Fruit color: Close to 144B. Seed length: Less than 1 mm. Seed diameter: Less than 1 mm.

Disease & pest resistance: Plants of the new *Buddleia* have not been observed to be resistant to pathogens and pests common to *Buddleia* plants.

Garden performance: Plants of the new *Buddleia* have been observed to have good garden performance and tolerate rain, wind and to be hardy to USDA Hardiness Zone 6.

It is claimed:

1. A new and distinct *Buddleia* plant named 'UCONNBD603' as illustrated and described.

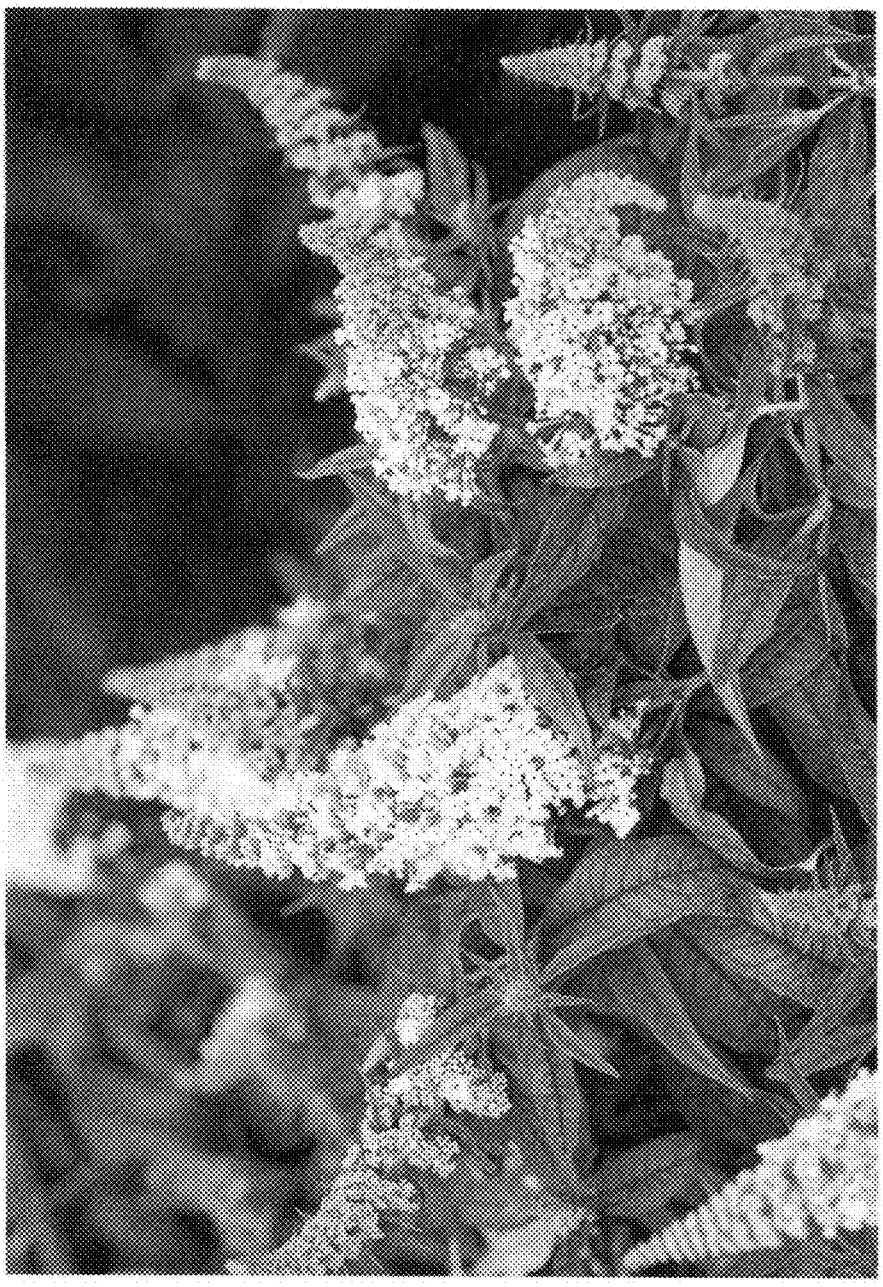

* * * * *